United States Patent
Tsung et al.

(10) Patent No.: US 9,293,659 B2
(45) Date of Patent: Mar. 22, 2016

(54) METHOD FOR FABRICATING MICROSTRUCTURE TO GENERATE SURFACE PLASMON WAVES

(71) Applicant: Cheng-Sheng Tsung, Nantou County (TW)

(72) Inventors: Cheng-Sheng Tsung, Nantou County (TW); Shih-Hao Chuang, Kaohsiung (TW)

(73) Assignee: CHENG-SHENG TSUNG, Caotun Township, Nantou County (TW)

( * ) Notice: Subject to any disclaimer, the term of this patent is extended or adjusted under 35 U.S.C. 154(b) by 0 days.

(21) Appl. No.: 14/694,553

(22) Filed: Apr. 23, 2015

(65) Prior Publication Data

US 2015/0228863 A1   Aug. 13, 2015

Related U.S. Application Data

(62) Division of application No. 14/244,460, filed on Apr. 3, 2014.

(30) Foreign Application Priority Data

Oct. 9, 2013   (TW) .............................. 102136489 A

(51) Int. Cl.
| | |
|---|---|
| *G02B 26/00* | (2006.01) |
| *G02F 1/00* | (2006.01) |
| *H01L 51/56* | (2006.01) |
| *H01L 33/60* | (2010.01) |
| *H01L 33/44* | (2010.01) |

(Continued)

(52) U.S. Cl.
CPC ............ *H01L 33/44* (2013.01); *B81C 1/00031* (2013.01); *G01N 21/01* (2013.01); *G02B 5/008* (2013.01); *H01L 33/60* (2013.01);

(Continued)

(58) Field of Classification Search
CPC ............ H01L 51/5262; H01L 51/5271; H01L 51/5268
USPC .................. 257/99, 40, 79, E33.068; 438/29; 427/421.1, 420, 430.1
See application file for complete search history.

(56) References Cited

U.S. PATENT DOCUMENTS

2008/0260941 A1 * 10/2008 Jin .............................. 427/126.4
2011/0109956 A1 * 5/2011 Hashimura et al. ........... 359/290

(Continued)

FOREIGN PATENT DOCUMENTS

| TW | I363440 | 5/2012 |
|---|---|---|
| TW | I395348 | 5/2013 |

*Primary Examiner* — Kimberly Rizkallah
*Assistant Examiner* — Brian Turner
(74) *Attorney, Agent, or Firm* — Muncy, Geissler, Olds & Lowe, P.C.

(57) ABSTRACT

A method for fabricating a microstructure to generate surface plasmon waves comprises steps of: preparing a substrate, and using a carrier material to carry a plurality of metallic nanoparticles and letting the metallic nanoparticles undertake self-assembly to form a microstructure on the substrate, wherein the metallic nanoparticles are separated from each other or partially agglomerated to allow the microstructure to be formed with a discontinuous surface. The present invention fabricates the microstructure having the discontinuous surface by a self-assembly method to generate the surface plasmon waves, thus exempts from using the expensive chemical vapor deposition (CVD) technology and is able to reduce the time and cost of fabrication. The present invention also breaks the structural limitation on generation of surface plasmon waves to enhance the effect of generating the surface plasmon waves.

5 Claims, 11 Drawing Sheets

(51) Int. Cl.
   *B81C 1/00*    (2006.01)
   *G02B 5/00*    (2006.01)
   *G01N 21/01*   (2006.01)

(52) U.S. Cl.
   CPC ..... *B81C2201/0149* (2013.01); *G01N 2201/02* (2013.01); *H01L 2933/0058* (2013.01)

(56) References Cited

U.S. PATENT DOCUMENTS

2011/0308598 A1* 12/2011 Girotto ............... 136/256
2012/0125430 A1* 5/2012 Ding et al. ............ 136/256
2013/0252275 A1* 9/2013 Tokonami et al. ......... 435/29

\* cited by examiner

METHOD FOR FABRICATING MICROSTRUCTURE TO GENERATE SURFACE PLASMON WAVES

CROSS REFERENCE TO RELATED APPLICATIONS

This application is a Divisional of co-pending application Ser. No. 14/244,460, filed on 3 Apr. 2014, for which priority is claimed under 35 U.S.C. §120; and this application claims priority of application Ser. No. 10/213,6489 filed in Taiwan on 9 Oct. 2013 under 35 U.S.C. §119, the entire contents of all of which are hereby incorporated by reference.

FIELD OF THE INVENTION

The present invention relates to a method for generating surface plasmon waves, particularly to a method for fabricating a microstructure to generate surface plasmon waves.

BACKGROUND OF THE INVENTION

Phenomenon of surface plasmon of metals has been widely used nowadays. Researchers find if a special metallic nanostructure is disposed on an interface between dielectric materials, it can generate an interaction between electromagnetic waves and the metallic nanostructure and result in many novel optical characteristic. The optical characteristic can be controlled via modifying the structure, size, relative position, periodical arrangement of the metallic nanostructures and types of the dielectric materials around the metallic nanostructures. Therefore, special nanostructures can be fabricated via controlling the parameters of the metallic nanostructures to generate desired surface plasmon resonances, which can be applied in many photoelectronic products, photoelectronic measurements and academic researches. In the current stage, the surface plasmon waves have been applied to many fields, such as Raman spectrom measurement, thin film thickness measurement, optics constant measurement, solar cells, optical sensors, and biological sensors.

Particularly, surface plasma can also be applied to increasing the light luminous efficiency of light emitting diode (LED). It was found that the surface plasma effect produced at the interface between the metallic nanostructure and the dielectric material can magnify the action of the electromagnetic field and generate near-field effect, thus enhancing the luminous efficiency of the nearby quantum dots or quantum wells and promoting the light luminous efficiency and brightness of solid-state LED.

Besides, light generated by recombination of electrons and holes in quantum wells is omnidirectional. Thus, only the light emitted towards a direction away from the substrate is applicable unless there is a light guiding mechanism, and the light emitted towards the direction needs to penetrate heterogeneous layers to reach the air. During penetration, optical reaction produced inside the heterogeneous layers will cause a portion of the emitted light to be constrained inside the heterogeneous layers and converted into another form of energy. As a result, the emitted light is decreased layer by layer. If a surface plasmon structure is disposed on the interface between the heterogeneous layer and the air, the energy lost in the optical reaction can be easily absorbed and coupled. The surface plasmon structure can convert the momentum loss into photons and radiate the photons. The above-mentioned phenomenon is the so-called Localized Surface Plasmon Resonance (LSPR).

A Taiwan patent No. I395348 discloses a "Semiconductor Light Emitting Element", which is an LED element having high light-emitting efficiency by using the technique of surface Plasmon. It discloses a metallic surface and a plurality of through-holes which are formed on the metallic surface and have a specified shape. Those through-holes are arranged in specified positions to form a metallic surface grating, which can excite generation of the surface plasma waves for achieving better light emitting efficiency.

Moreover, A Taiwan patent No. I363440 discloses "Light Emitting Element, Light Emitting Diode and Method for Fabricating the Same". Briefly, an LED structure of this patent includes a surface plasmon coupling unit to generate surface plasmon waves and increase the luminous efficiency of LED.

The abovementioned conventional methods for fabricating specific nanostructures to generate surface plasma waves normally use technologies such as vapor deposition, sputtering coating, photo masks, pattern development and etching to form a plurality of metallic nanostructure regions, and then perform annealing process to transform the metallic nanostructure regions into spherical structures by the effect of surface tension. Therefore, the abovementioned conventional methods are complicated and expensive.

Besides, surface plasmon may be categorized into Surface Plasmon Polaritons (SPP) and Localized Surface Plasmon (LSP). The SSP exists on the interface between a metallic material and a dielectric material, wherein the LSP exists in a metallic nanostructure by a resonance mode. So far, the conventional technology is unable to apply the SSP and the LSP techniques in an identical systematic structure. The conventional technology is either unable to provide a cheaper process to generate the SSP and the LSP simultaneously.

In the conventional technology, surface plasmon can only exist in an interface between a metallic material and a dielectric material, which considerably constrains the design of surface plasmon generation structures. Therefore, the conventional technology still has room to improve.

SUMMARY OF THE INVENTION

The primary objective of the present invention is to improve the conventional technology that must uses the expensive and time-consuming Chemical Vapor Deposition (CVD) process to undertake the deposition of a continuous metallic structure for generating surface plasmon waves.

Another objective of the present invention is to overcome the structural limitation which limit the generation of surface plasmon waves by forming a 3D surface plasmon generation structure, so as to enhance function of the surface plasmon waves and achieve complex surface plasmon waves effect.

To achieve the abovementioned objectives, the present invention proposes a method for fabricating a microstructure to generate surface plasmon waves, which comprises steps of:

Step S1: preparing a substrate; and

Step S2: using a carrier material to carry a plurality of metallic nanoparticles and letting the metallic nanoparticles undertake self-assembly to form a microstructure on the substrate, wherein the plurality of metallic nanoparticles are separated from each other or partially agglomerated to allow the microstructure to be formed with a "discontinuous surface".

The present invention features in using a self-assembly method to let the metallic nanoparticles be separated from each other or partially agglomerated to fabricate the microstructure with a discontinuous surface for generating surface plasmon waves. The present invention is exempted from using the expensive CVD process and has advantages of low fabrication cost and short fabrication time.

DETAILED DESCRIPTION OF THE PREFERRED EMBODIMENTS

The present invention will be described in detail in cooperation with the drawings below.

Figure 1:
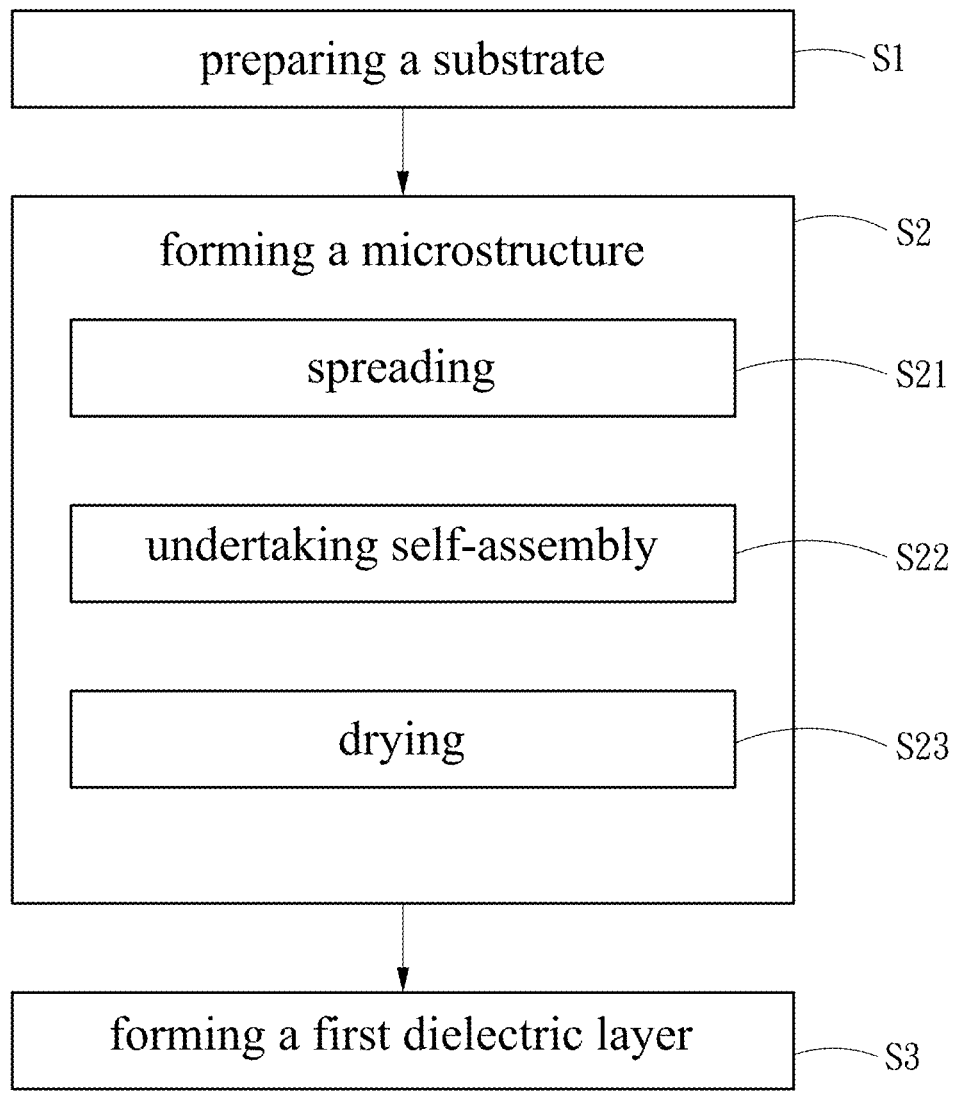
FIG. 1 is a flowchart of a method for fabricating a microstructure to generate surface plasmon waves according to a first embodiment of the present invention.
Figure 2A:
FIGS. 2A-2D are sectional views schematically showing the steps of fabricating the microstructure to generate the surface plasmon waves according to the first embodiment of the present invention.

Referring to FIGS. 1 and 2A-2D, the present invention proposes a method for fabricating a microstructure to generate 3 Dimensional (3D) complex surface plasmon waves. The method of the present invention comprises the steps of:

Step S1: preparing a substrate 10, as shown in FIG. 2A. According to different requirements, the substrate 10 may be a electrooptic element (such as a solar cell, an optical sensor, or an LED), a single layer film, or a multilayer film.

Figure 2B:
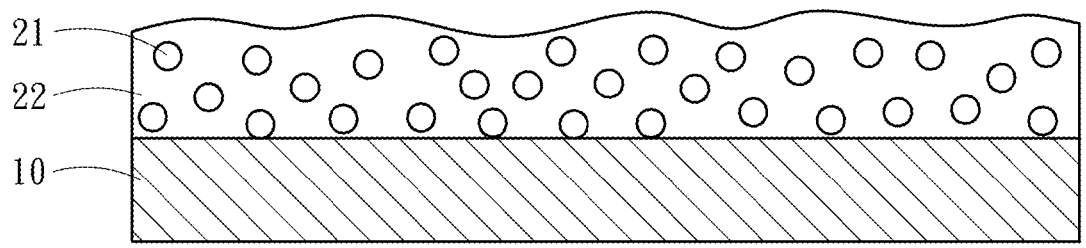
Figure 2C:
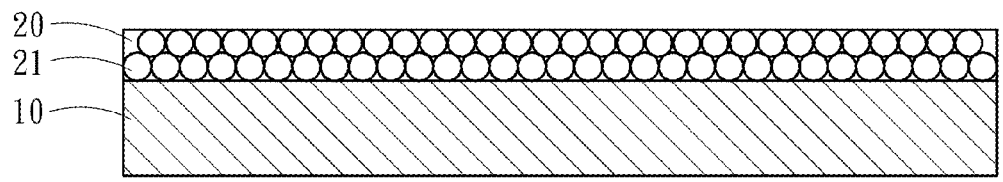

Step S2: forming a microstructure, as shown in FIG. 2B. A carrier material 22 is used to carry a plurality of metallic nanoparticles 21 to form a microstructure on the substrate 10 in a self-assembly way. The metallic nanoparticles 21 are separated from each other or partially agglomerated to allow the microstructure to be form with a discontinuous surface. The carrier material 22 could be a solid material, a liquid material or a gaseous material. The metallic nanoparticles 21 may be made of a material selected from a group consisting of gold, silver, aluminum, compounds thereof, alloys thereof and mixtures thereof. The metallic nanoparticles 21 are uniformly distributed in the carrier material 22. In this embodiment, the concentration of the metallic nanoparticles 21 in the carrier material 22 is less than 5000 ppm, and the metallic nanoparticles 21 are formed at a particle size ranged between 1 nm and 100 nm. After adding oxides and mixtures, the particle size of the metallic nanoparticle 21 may greater than 100 nm. In the present invention, the discontinuous surface is formed by the metallic nanoparticles 21 that are separated from each other or partially agglomerated. Since that, the discontinuous surface of the present invention is different from the "continuous surface" formed by the CVD process, and the performance of the discontinuous surface is quite different from the performance of the continuous surface. It should be particularly mentioned that only the microstructure formed with the discontinuous surface which consists of nanometric metallic particles that are distributed in a separated way or a partially-agglomerated way could be realized as the microstructure to generate the surface plasmon waves of the present invention.

In a first embodiment of the invention, the carrier material 22 is a volatile liquid such as acetone (ACE) or isopropanol (IPA), and the Step S2 further comprises the following steps of:

Step S21: spreading. The carrier material 22 and the metallic nanoparticles 21 carried by the carrier material 22 are spread on the substrate 10 via a spin-coating method, a spraying method, a drip-coating method, or a soaking method, as shown in FIG. 2B;

Step S22: undertaking self-assembly. The metallic nanoparticles 21 move mutually in the carrier material 22 to form a plurality of two dimensional hexagonal close packed (2D HCP) structures via self-assembly, i.e. the metallic nanoparticles 21 are partially agglomerated to form a plurality of planar sheet structures.

Step S23: drying. A drying process is undertaken to gradually volatilize the carrier material 22. Thus, the 2D HCP structures are stacked on one another to form a metallic particle stacking layer 20, i.e. the microstructure with the discontinuous surface. The drying temperature is below 500° C., preferably between 95° C. and 170° C. The drying time is less than 1 hour, preferably between 30 seconds to 5 minutes.

In the first embodiment, the Step S21 is performed by a spin-coating process. The spin-coating process can remove the residual metallic nanoparticles 21 without being arranged from the surface of a wafer and makes the film have a uniform thickness. A film with uniform thickness will be obtained via spin-coating the carrier material 22 and the metallic nanoparticles 21 at an appropriate rotation speed for an appropriate time. In this embodiment, the rotation speed of the spin-coating is below 8000 rpm to allow the metallic nanoparticles 21 to form the metallic particle stacking layer 20. In fact, the rotation speed of spin-coating correlates with the thickness and uniformity of the film, and the concentration of the metallic nanoparticles 21 correlates with the electric properties, optical properties, electric field and magnetic field effect and thickness.

Figure 2D:
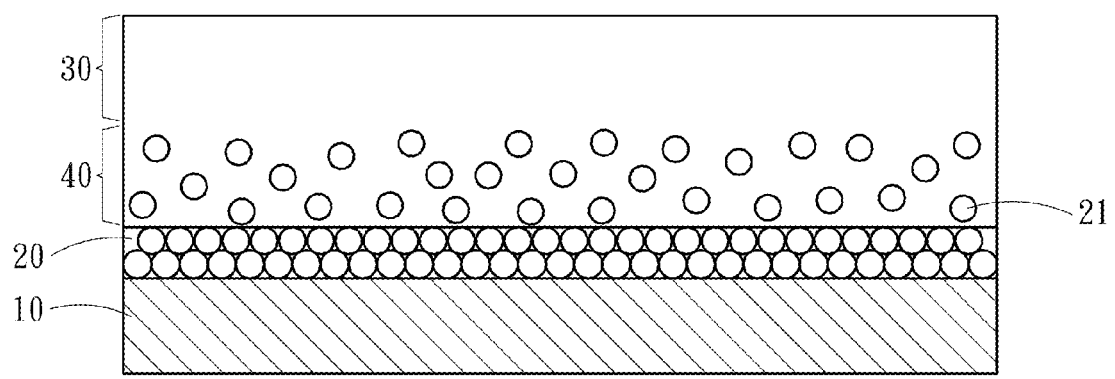

Then, the metallic particle stacking layer 20 is used to generate the surface plasmon waves. In order to eliminate the limitation on the generation of surface plasmon waves, the method of the present invention further comprises:

Step S3: forming a first dielectric layer 30. As shown in FIG. 2D, the first dielectric layer 30 is formed on one side of the metallic particle stacking layer 20 far away from the substrate 10. The first dielectric layer 30 is made of a material selected from a group consisting of Indium Tin Oxide (ITO), Aluminum Zinc Oxide (AZO) and Zinc Oxide (ZnO). Afterwards, the metallic nanoparticles 21 of the metallic particle stacking layer 20 enter the first dielectric layer 30 by absorption or diffusion to form a first particle suspension layer 40. The first dielectric layer 30 is formed by a process such as an electron beam vapor deposition method, an ion beam vapor deposition method, a laser coating method, an epitaxial coating method, or a plasma-enhanced chemical vapor deposition method. Thereby, some optical effect such as diffraction, refraction and total reflection will occur at a specified wavelength range to form Attenuated Total Reflection (ATR), which can enhance the coupling mechanism of the surface plasmon waves.

The metallic particle stacking layer 20 and the first particle suspension layer 40 can respectively generate the SPP and the LSP. Further, the near-field effect will cause resonance of the SPP and the LSP to enhance the surface plasmon waves, which makes the SPP and the LSP be abbreviated as SP-SP. Therefore, the metallic particle stacking layer 20 and the first particle suspension layer 40 may serve as a structure to generate a 3D complex surface plasmon waves.

Figure 3A:
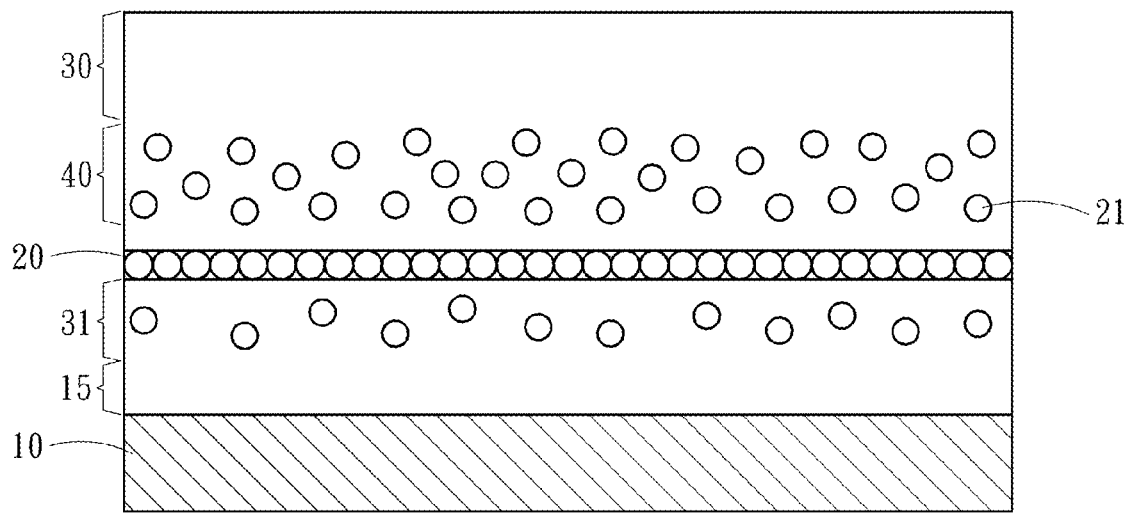
FIG. 3A is a sectional view schematically showing a microstructure fabricated according to a second embodiment of the present invention.
Figure 3B:
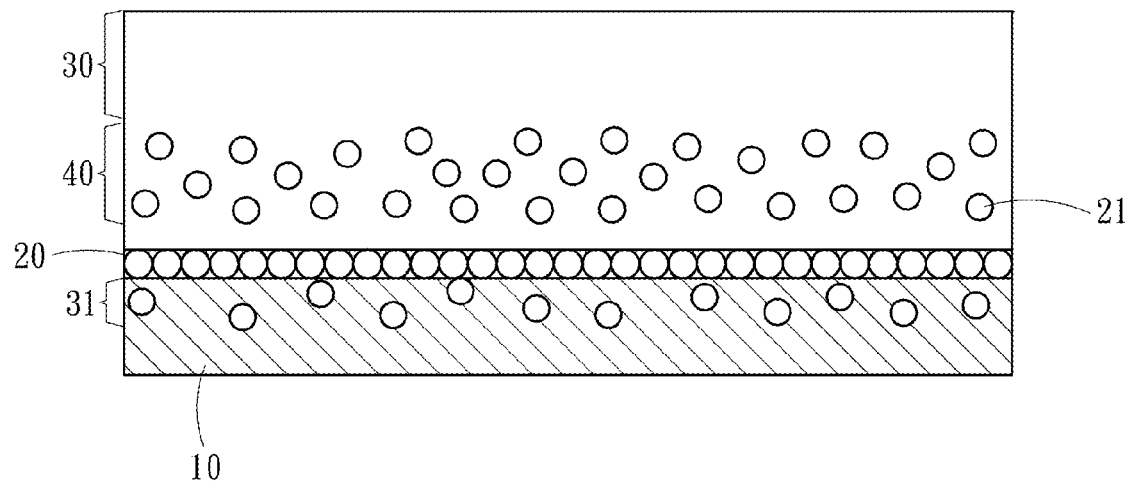
FIG. 3B is a sectional view schematically showing another microstructure fabricated according to the second embodiment of the present invention.

In addition to the first particle suspension layer 40 formed on the one side of the metallic particle stacking layer 20 far away from the substrate 10, another particle suspension layer may also be formed on one side of the metallic particle stacking layer 20 close to the substrate 10 via activating the substrate 10. FIG. 3A shows a second embodiment of the present invention, wherein the substrate 10 in the Step S1 includes a second dielectric layer 15 on the surface thereof. In the succeeding step of fabricating the metallic particle stacking layer 20, the metallic nanoparticles 21 enter the second dielectric layer 15 by absorption or diffusion, so as to form a second particle suspension layer 31. Alternatively, as shown in FIG. 3B, the substrate 10 is activated via heating the substrate 10 to a temperature of 500-600° C., or compressed with the metallic particle stacking layer 20 at a temperature of 280° C. and under a pressure of 500 Kg/cm$^2$, so that the metallic nanoparticles 21 may enter the substrate 10 to form a third particle suspension layer 32. Both the second particle suspension layer 31 and the third particle suspension layer 32 are formed on the substrate 10 to serve the same function.

In one embodiment, under one condition that the metallic particle stacking layer 20 is not formed, via adjusting the concentration of the metallic nanoparticles 21 the metallic nanoparticles 21 can enter the substrate 10 or the first dielectric layer 30 by absorption or diffusion to form the second particle suspension layer 31 or the first particle suspension layer 40.

Figure 4:
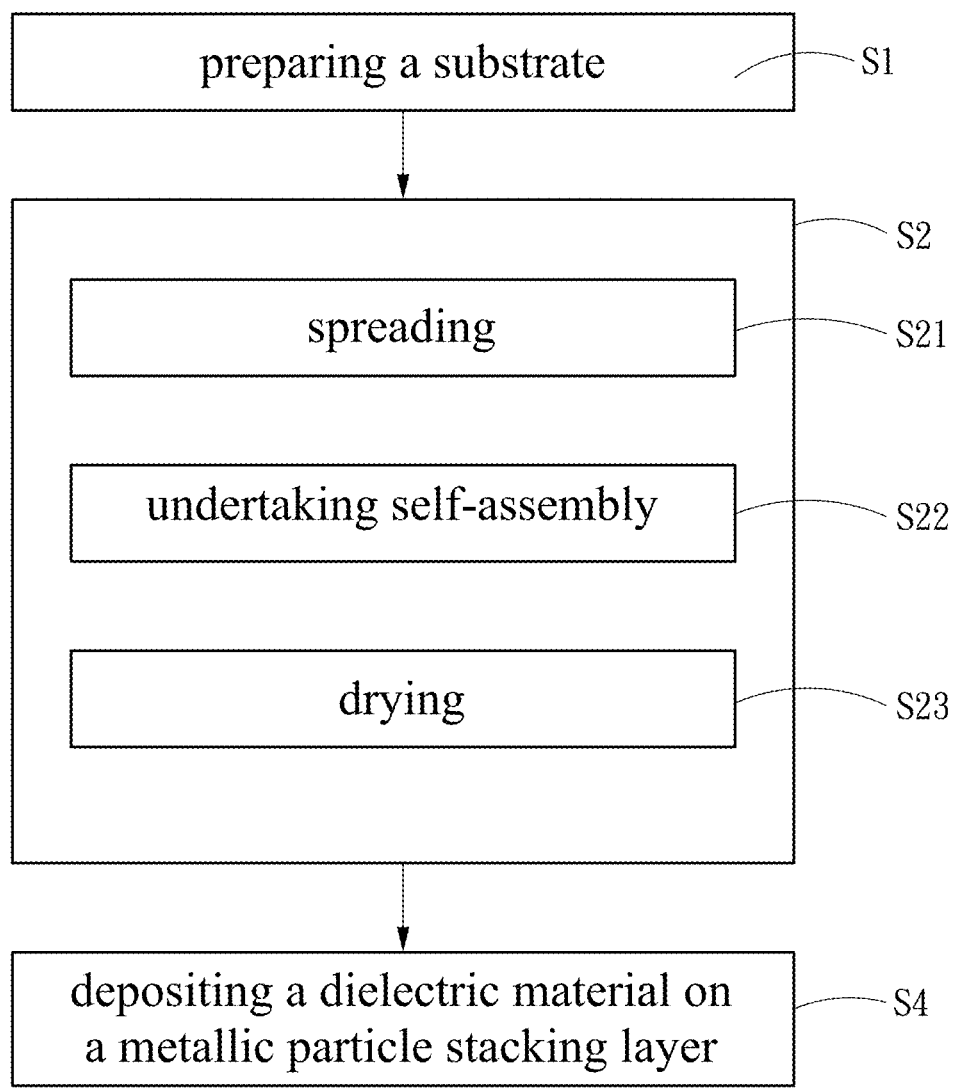
FIG. 4 is a flowchart according to a third embodiment of the present invention.
Figure 5:
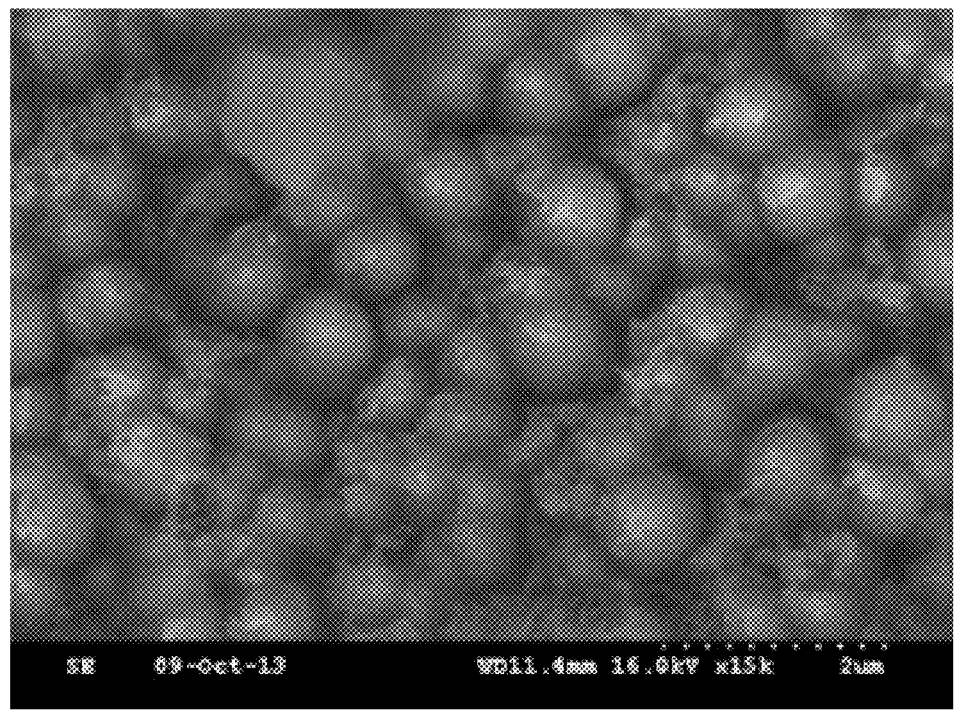
FIG. 5 is a SEM image of the microstructure fabricated according to the third embodiment of the present invention.

Please refer to FIG. 4 for a third embodiment of the present invention, wherein metallic spherical structures are formed. In the Step S1, preparing a substrate 10 having a plurality of grooves (not shown in the drawings). After the Step S2, the process directly proceeds to Step S4: depositing a dielectric material on the metallic particle stacking layer 20. Then, the metallic nanoparticles 21 will wrap the dielectric material by self-assembly and form a plurality of spherical structures which are able to generate the surface plasmon waves. Refer to FIG. 5 for the scanning electron microscopy (SEM) image of the spherical structures.

In the present invention, the metallic particle stacking layer 20 can generate the SPP. Also, the first particle suspension layer 40 includes the dielectric material and the metallic nanoparticles 21 which enter the dielectric material from the surface of the metallic particle stacking layer 20 by chemical absorption or physical diffusion, namely, in a self-assembly way. Therefore, the surface plasmon wave generated at the first particle suspension layer 40 may be regarded as the LSP. Thus, through cooperation of the metallic particle stacking layer 20 and the first particle suspension layer 40 complex surface plasmon waves can be generated. Therefore, the microstructure of the present invention can generate the surface plasmon waves in a coupled resonance mode of the SPP and the LSP. According to the theory of surface plasmon, a TE polarized light is unable to generate the surface plasmon waves because its electric field is vertical to the incident plane, but a TM polarized light has a electric field parallel to the incident plane and thus it is able to form continuous waves and generate the surface plasmon waves. As such, lights with wavelength outside a absorption wavelength range of the microstructure of the invention can directly penetrate the microstructure, and non-absorbable lights with wavelength in the absorption wavelength range, i.e. the TE polarized light and the residual TM polarized light that is not absorbed because of absorption saturation, also directly penetrates the structure. For the absorbed lights, because the metallic particle stacking layer 20 and the first particle suspension layer 40 of the present invention generate the surface plasmon waves in the coupled resonance mode, they are converted to the TE polarized light and emitted from the microstructure.

Figure 6:
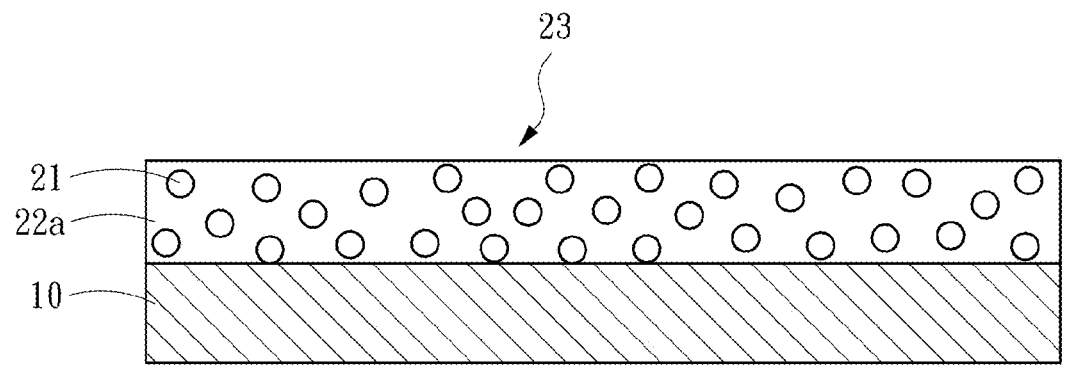
FIG. 6 is a sectional view schematically showing the microstructure fabricated according to a fourth embodiment of the present invention.

Please refer to FIG. 6 for a fourth embodiment of the present invention, in which a particle suspension structure is directly formed by modifying the fabrication parameters. In the Step S2, the carrier material 22a is a non-volatile liquid that would not vaporize or volatilize. The metallic nanoparticles 21 are uniformly distributed in the carrier material 22a. The carrier material 22a and the metallic nanoparticles 21 carried by the carrier material 22a are spread on the substrate 10 via a spin-coating method, a spraying method, a drip-coating method, or a soaking method, and then the carrier material 22a is cured via baking or natural drying to form a nanoparticle suspension film 23, i.e. the discontinuous surface of the microstructure of the present invention. The nanoparticle suspension film 23 fabricated thereby can also generate the surface plasmon waves. It should be particularly mentioned that in the third embodiment, the mutual movements of the metallic nanoparticles 21 cause them to be separated from each other, so as to form the discontinuous surface of the microstructure of the present invention.

The 3D complex surface plasmon waves generated by the abovementioned embodiments can be applied in various industries, such as to increasing the luminous efficiency of LED and the photoelectric conversion efficiency of solar cells.

Figure 7A:
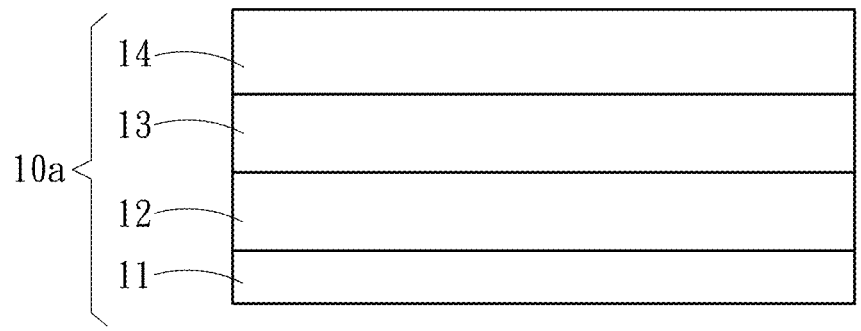
FIGS. 7A-7E are sectional views schematically showing the steps of fabricating an LED structure with the microstructure of the present invention.

Take application of LED for instance, a light emission path of an LED is from the substrate 10 through the metallic particle stacking layer 20 and the first particle suspension layer 40 to the first dielectric layer 30. Lights passing through the light emission path can be purified consecutively to increase the ratio of the TE polarized light and the light extraction efficiency, and to decrease the structure-induced light energy loss. If the light emission path has a reverse sequence, it can also achieve the same effect. Please refer to FIGS. 7A-7E. The fabrication of a horizontal type surface plasmon LED is used to exemplify the present invention below. The process includes the following steps of:

Step P1: preparing a substrate 10a, which is an LED structure including a substrate 11, an N-type semiconductor layer 12, an multiple quantum well (MQW) layer 13 and a P-type semiconductor layer 14, as shown in FIG. 7A. The substrate 10a is cleaned in this step.

Figure 7B:
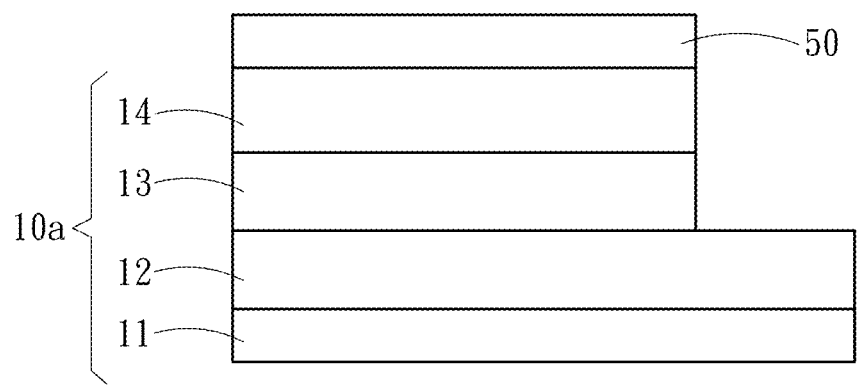

Step P2: using a photolithography process and a photoresist layer 50 to form a pattern and undertaking etching to form a platform, as shown in FIG. 7B. In this step, an Inductively Coupled Plasma-Reactive Ion Etching (ICP-RIE) process is used to undertake etching. Then, removing the photoresistor layer 50 and cleaning the substrate 10a.

Figure 7C:
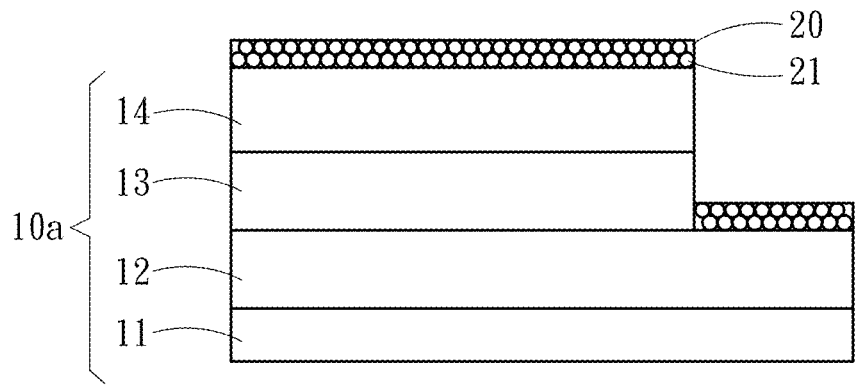

Step P3: forming a coating including the metallic nanoparticles 21, as shown in FIG. 7C. The carrier material 22 and the metallic nanoparticles 21 carried by the carrier material 22 are spread on the substrate 10a via the spin-coating method, the spraying method, the drip-coating method, or the soaking method. The carrier material 22 is selected from a group consisting of ACE, IPA, volatile solvents, and other solvents having low-boiling point. The metallic nanoparticles 21 are made of gold, silver, aluminum, or oxides thereof, and the metallic nanoparticles 21 can be a single-material type or a multi-material type. The coating is dried via baking to remove the carrier material 22 and form the metallic particle stacking layer 20.

Figure 7D:
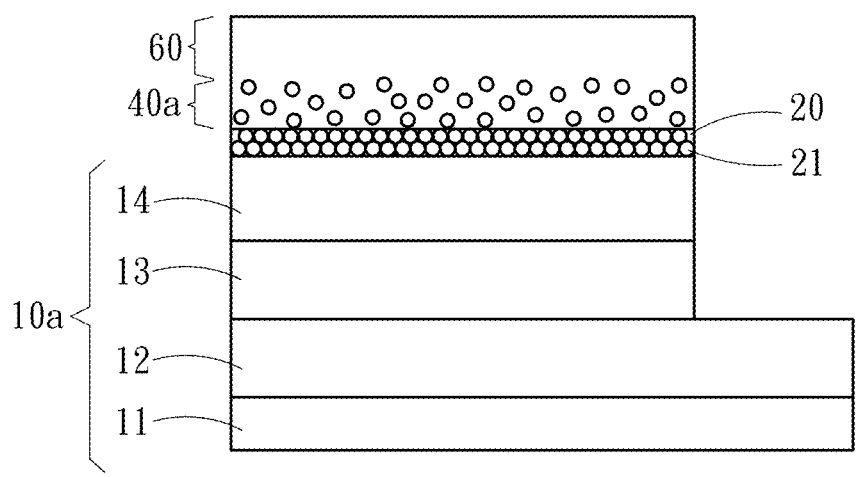

Step P4: forming a transparent conductive layer 60 on one side of the metallic particle stacking layer 20 away from the substrate 10a, as shown in FIG. 7D. The transparent conductive layer 60 is formed via the electron beam vapor deposition method, the ion beam vapor deposition method, the laser coating method, the epitaxial coating method, or the plasma-enhanced chemical vapor deposition method. The transparent conductive layer 60 can induce some optical effect, such as diffraction, refraction and total reflection, at the specified wavelength range to form the ATR, which can enhance the coupling mechanism of the surface plasmon waves. In addition, the metallic nanoparticles 21 could enter the transparent conductive layer 60 by absorption or diffusion, and through the self-assembly mechanism thereof to from the first particle suspension layer 40a on one side of the transparent conductive layer 60 adjacent to the metallic particle stacking layer 20. Then, the metallic particle stacking layer 20 cooperates with the first particle suspension layer 40a to generate a complex surface plasmon wave.

Figure 7E:
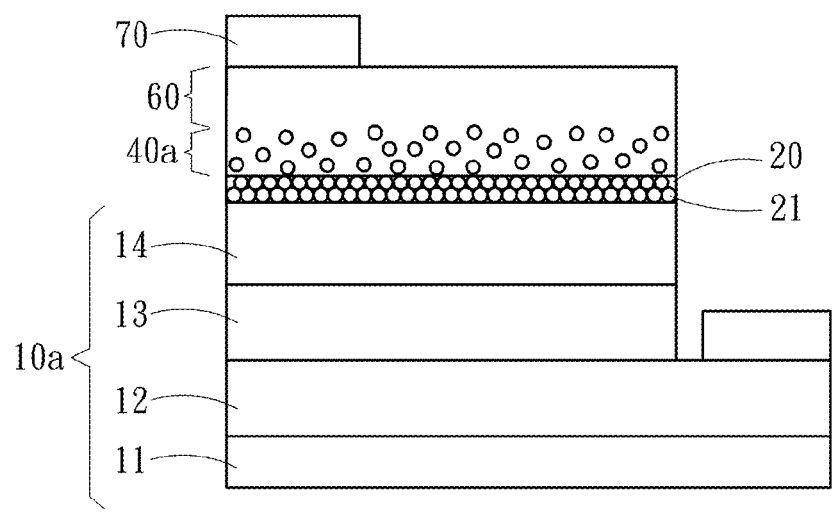

Step P5: fabricating electrodes 70. As shown in FIG. 7E, two electrodes 70 are respectively formed on the transparent conductive layer 60 and the N-type semiconductor layer 12 to form the LED structure.

Figure 8:
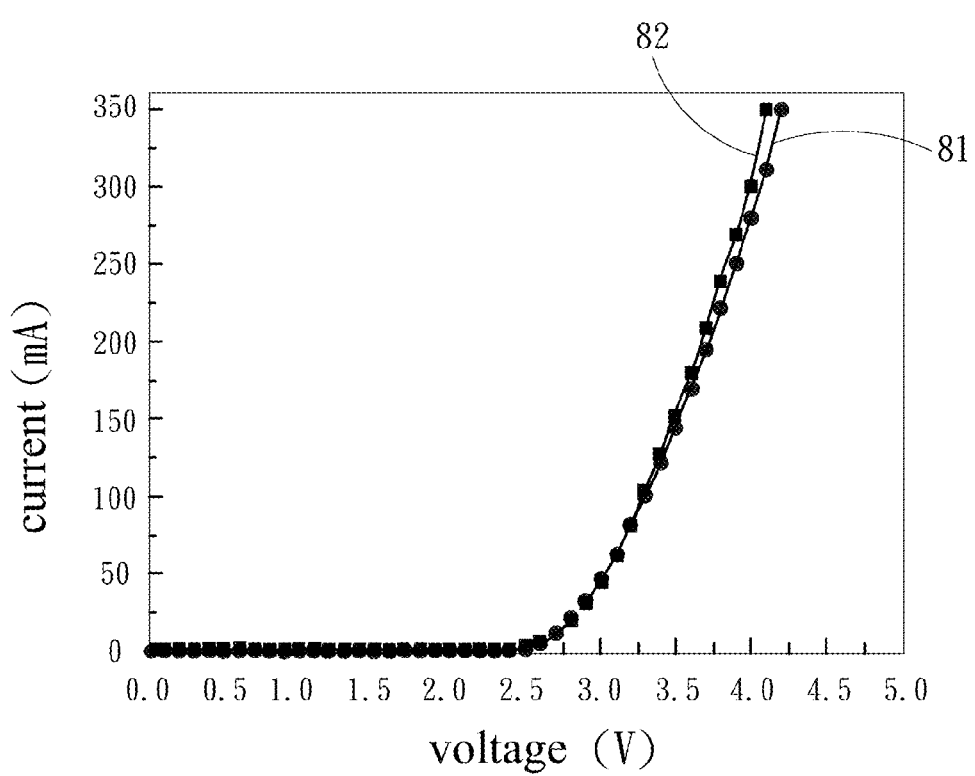
FIG. 8 shows the I-V curves of an ordinary LED and a surface plasmon LED fabricated according to the method of the present invention.
Figure 9A:
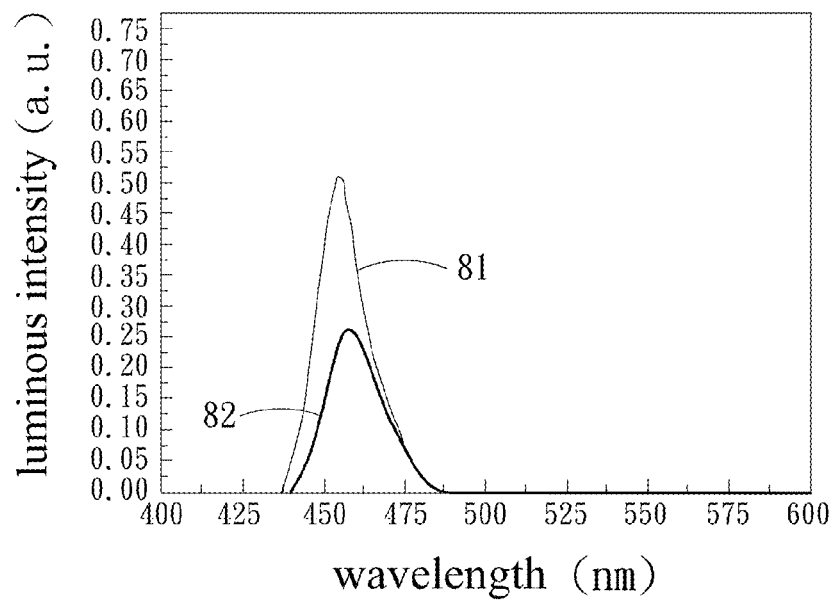
FIG. 9A shows light emitting efficiency curves of the ordinary LED and the surface plasmon LED at a current of 20 mA.
Figure 9B:
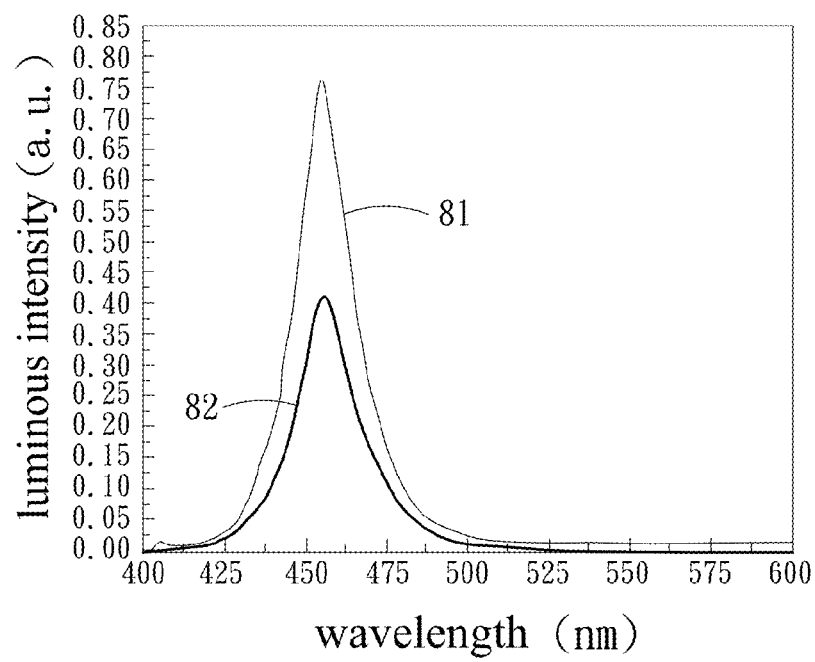
FIG. 9B shows the light emitting efficiency curves of the ordinary LED and the surface plasmon LED at a current of 350 mA.

FIG. 8 shows curves of the current-voltage (I-V) relationships of an ordinary LED 82 and a surface plasmon LED 81 fabricated according to the present invention and having the microstructure to generate the 3D complex surface plasmon waves. It is observed that there is no much difference between the I-V curve of the surface plasmon LED 81 and that of the ordinary LED 82. Please further refer to FIG. 9A and FIG. 9B for the light emitting efficiencies which are respectively performed at a current of 20 mA and 350 mA. It is observed in FIG. 9A and FIG. 9B that the light emitting efficiency of the surface plasmon LED 81 of the present invention is much better than that of the ordinary LED 82. The present invention indeed uses the complex surface plasmon technology to increase the light emitting efficiency of LED.

Figure 10:
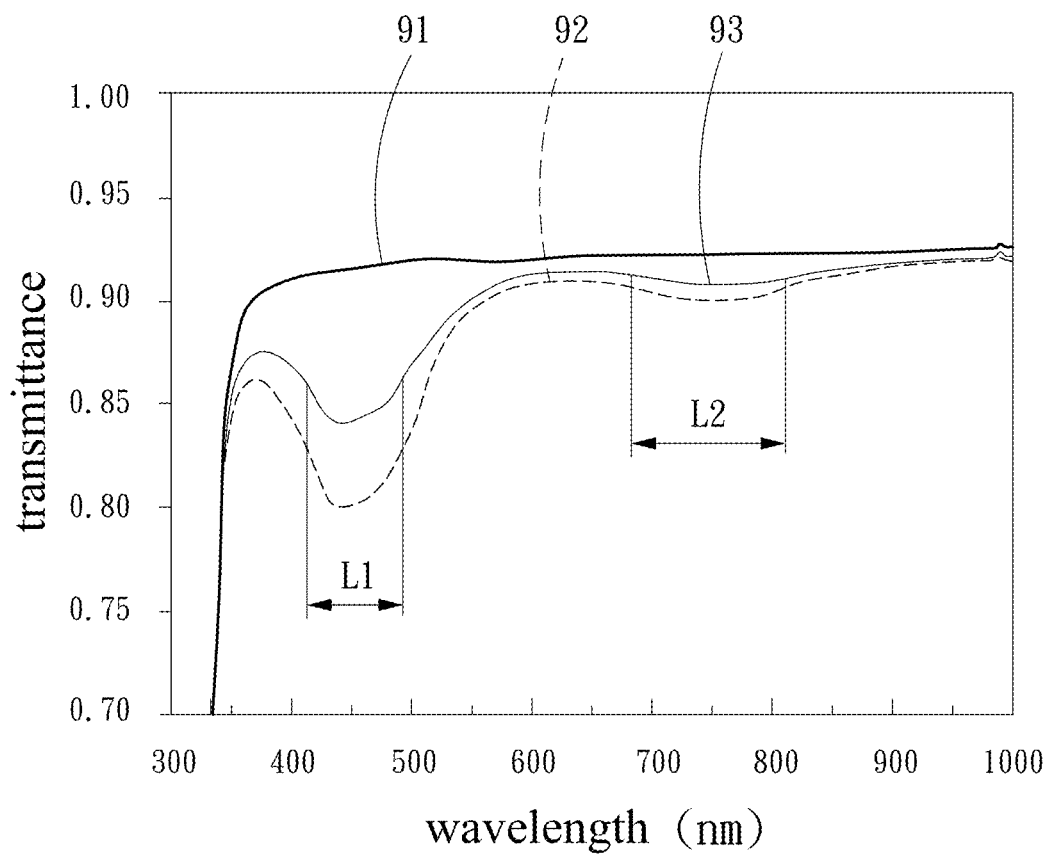
FIG. 10 shows light transmittance curves of microstructures fabricated at different rotation speed.

FIG. 10 shows curves light transmittances of the microstructure of the present invention respect to light wavelength which also imply the light absorption rates. A comparison curve 91 is the transmittance-wavelength relationship of an LED structure unable to generate the surface plasmon waves. A low rotation speed curve 92 is the transmittance-wavelength relationship of the metallic particle stacking layer 20 fabricated at a low rotation speed in the spin-coating process. A high rotation speed curve 93 is the transmittance-wavelength relationship of the metallic particle stacking layer 20 fabricated at a high rotation speed in the spin-coating process. The metallic particle stacking layer 20 fabricated at the low rotation speed (the low rotation speed curve 92) has a thickness greater than that of the metallic particle stacking layer 20 fabricated at the high rotation speed (the high rotation speed curve 93). Both the low rotation speed curve 92 and the high rotation speed curve 93 obviously chows the same two light absorption areas L1 and L2, which respectively represent the absorption phenomena of the SPP and the LSP. Therefore, FIG. 10 indicates that the structures of the present invention indeed can generate both the SPP and the LSP, i.e. the present invention can indeed generate the 3D complex surface plasmon waves. In this embodiment, the low rotation speed is 2000 rpm, and the high rotation speed is 4000 rpm.

In conclusion, the present invention has the following characteristics:

1. The present invention does not use any expensive deposition process but uses the self-assembly technology to form a microstructure for generating the surface plasmon waves.
2. The present invention uses the metallic nanoparticles of the metallic particle stacking layer to form the first particle suspension layer. Both the metallic particle stacking layer and the first particle suspension layer can generate the surface plasmon waves. Thus, the present invention can break the limitation of the conventional structure for the generation of the surface plasmon waves to generate the 3D complex surface plasmon waves. Therefore, the present invention can enhance the effency of generating the surface plasmon waves.
3. The present invention uses the spin-coating method, the spraying method, the drip-coating method, or the soaking method to form the metallic particle stacking layer, whereby the succeeding first particle suspension layer can be easily formed, so that the fabrication cost can be effectively reduced.
4. The present invention can vary the fabrication parameters to form the metallic particle stacking layer, the first particle suspension layer, the second particle suspension layer, the third particle suspension layer, the spherical structures, or the nanoparticle suspension film to meet different requirements.
5. The present invention uses the coupling effect of the surface plasmon waves to increase the output ratio of the TE polarized light and thus can be applied in a field of filter film.
6. The present invention can undertake an etching process together with the spin-coating process, the spraying process, or the soaking process, thus can greatly reduce the cost and complexity of fabrication and has high commercial potential.
7. The structure of the present invention can convert the light energy, which is confined in the LED structure and unused originally, into output light having directivity, so as to reduce the light energy loss.
8. The metallic particle stacking layer and the first particle suspension layer respectively generate the SPP and the LSP. Thus, the metallic particle stacking layer cooperates with the first particle suspension layer to form an SP-SP structure. Therefore, the present invention can enhance the effect of the surface plasmon waves.
9. The surface plasmon waves generated by the absorbed incident light are transformed into photons. The photons are re-emitted and mixed with the unabsorbed incident light to generate the light mixing effect.
10. The technique of present invention, through varying the fabrication parameters such as the type of the solvent, the size of particles or the concentration of particles and modifying the environmental factors, can be used to fabricate solid-state quantum processors, solid-state magnetic materials, or surface plasmon photonic crystals.
11. The microstructure of present invention be used to perform a stripping process at an appropriate temperature through increasing the concentration of the metallic nanoparticles in the carrier material.
12. The surface plasmon waves made of different metals have different absorption and emission wavelength range. The lights emitted by the surface plasmon waves of made one metal may serve as incident lights and being absorbed by the surface plasmon waves made of another metal. Furthermore, the metallic nanoparticles may be a single-metal type or a multi-metal typeto generate the mixed light having the required wavelength.

13. The metallic particle stacking layer and the first dielectric layer can be peeled off and overlay on another substrate to generate the surface plasmon waves on another substrate.

What is claimed is:

1. A method for fabricating a microstructure to generate surface plasmon waves, comprising the steps of:
    Step S1: preparing a substrate;
    Step S2: using a volatile liquid to carry a plurality of metallic nanoparticles, and letting the metallic nanoparticles undertake self-assembly to form a microstructure on the substrate, wherein the plurality of metallic nanoparticles are separated from each other or partially agglomerated to allow the microstructure to be formed with a discontinuous surface, and wherein the Step S2 further includes the steps of:
    Step S21: spreading the volatile liquid and the metallic nanoparticles carried by the volatile liquid on the substrate via a spin-coating method, a spraying method, a drip-coating method, or a soaking method;
    Step S22: letting the metallic nanoparticles move mutually in the volatile liquid to form a plurality of two dimensional hexagonal close packed (2D HCP) structures via self-assembly; and
    Step S23: undertaking a drying process to gradually volatilize the volatile liquid to make the 2D HCP structures be stacked on another to form a metallic particle stacking layer serving as the discontinuous surface of the microstructure; and
    Step S3: forming a first dielectric layer on one side of the metallic particle stacking layer far away from the substrate, and letting the metallic nanoparticles of the metallic particle stacking layer enter the first dielectric layer by absorption or diffusion to form a first particle suspension layer.

2. The method for fabricating the microstructure to generate the surface plasmon waves according to claim 1, wherein the volatile liquid is acetone or isopropanol.

3. The method for fabricating the microstructure to generate the surface plasmon waves according to claim 1, wherein the first dielectric layer is made of a material selected from a group consisting of Indium Tin Oxide (ITO), Aluminum Zinc Oxide (AZO) and Zinc Oxide (ZnO).

4. The method for fabricating the microstructure to generate the surface plasmon waves according to claim 1 further comprising Step S4: depositing a dielectric material on the metallic particle stacking layer and letting the metallic nanoparticles wrap the dielectric material via self-assembly and form a plurality of spherical structures that is performed after the Step S2, and wherein in the Step S1, the substrate includes a plurality of grooves.

5. The method for fabricating the microstructure to generate the surface plasmon waves according to claim 1, wherein in the Step S2, the metallic nanoparticles enter the substrate by absorption or diffusion to form a third particle suspension layer.

* * * * *